US00PP13384P3

(12) United States Plant Patent
Lipka

(10) Patent No.: US PP13,384 P
(45) Date of Patent: Dec. 17, 2002

(54) 'KRISTIN LIPKA'S VARIEGATED WEEPING DOGWOOD TREE'

(76) Inventor: Robert Lipka, P.O. Box 106, Cedars, PA (US) 19423

( * ) Notice: Subject to any disclaimer, the term of this patent is extended or adjusted under 35 U.S.C. 154(b) by 12 days.

(21) Appl. No.: 09/845,701

(22) Filed: Apr. 30, 2001

(65) Prior Publication Data

US 2002/0162148 P1 Oct. 31, 2002

(51) Int. Cl.[7] ..... A01H 5/00
(52) U.S. Cl. ..... Plt./220
(58) Field of Search ..... Plt./220

(56) References Cited

U.S. PATENT DOCUMENTS

PP11,654 P * 11/2000 Asako ..... Plt./220

* cited by examiner

*Primary Examiner*—Bruce R. Campell
*Assistant Examiner*—Anne Marie Grünberg
(74) *Attorney, Agent, or Firm*—Robert Lipka

(57) ABSTRACT

A new and distinct cultivar of *Cornus Kousa* Pendula known as 'Kristin Lipka's Variegated Weeper' as illustrated and described. This new cultivar has the distinction of being variegated and having a strong weeping habit.

4 Drawing Sheets

BACKGROUND OF THE INVENTION

The present invention relates to a new and distinct cultivar of Kousa Dogwood botanically known as *Cornus Kousa*, and hereinafter referred to by the cultivar name 'Kristin Lipka's Variegated Weeper'.

The new Kousa Dogwood was discovered in a nursery row by the Inventor in a cultivated area in Cedars, Pa., as a naturally occurring branch sport of a plant of an unnamed variety of *Cornus Kousa* Pendula. This unnamed variety is described as having solid green (nonvariegated) leaves. The selection of this branch sport was based on its unique variegated foliage.

Asexual reproduction of the new Weeping Kousa Dogwood by grafting, has shown that the unique features of this new Weeping Kousa Dogwood are stable and reproduced true to type in successive generations.

BRIEF SUMMARY OF THE INVENTION

Plants of the new Kousa Dogwood have not been observed under all possible environmental conditions. The phenotype may vary somewhat with the variations in environment such as temperature, day length, light intensity, nutrition and water status without, however, any variance in genotype. Color notations of the variegated leaves, stems, flowers, and flower buds are determined by the usage of The Royal Horticultural Society Colour Chart. These color references are being conducted in April under environmentaly controlled (heated greenhouse) conditions. Growth rate during the early stages (new grafts) cannot be fully determined due to the time of the year. The growth rate of the parent plant, with the variegated weeping branch sport, growing in the field is typical of a Weeping Kousa Dogwood. It is approximately 10 yrs old and its dimensions are 8' high and 5' wide with a strong weeping habit. This description is as complete as is reasonably possible.

DETAILED BOTANICAL DESCRIPTION

The following observations, measurements, values and comparisons describe plants grown in Cedars, Pa., under both outdoor and heated greenhouse conditions, which closely approximate commercial production conditions. Plants used for this description are fresh grafts and two year old field grown grafts.

Botanical classification: *Cornus Kousa*; cultivar 'Kristin Lipka's Variegated Weeper'.

Parentage: Naturally occurring branch sport of an unnamed variety of *Cornus Kousa* Pendula described as having solid green (nonvariegated) leaves.

PROPAGATION

Type: By grafting scions on to *Cornus Kousa* seedlings (understock). This is done in January using dormant scions on actively growing seedlings.

Rooting ability has not been determined at this date due to limited plant material.

The following traits have been repeatedly observed and are determined to be the unique characteristics of 'Kristin Lipka's Variegated Weeper'. The characteristics in combination distinguish 'Kristin Lipka's Variegated Weeper' as a new and distinct cultivar.

1. Medium to vigorous growth rate during early stages, slowing at maturity.
2. Large leaves (measurements and color given later) with unique green and white variegated foliage.

The new Weeping Variegated Dogwood differs from the parent variety of *Cornus Kousa* Pendula primarily in leaf coloration as plants of the new Weeping Dogwood have variegated leaves whereas plants of the parent variety have nonvariegated, solid green leaves.

As of this date and to my knowledge, there are no known weeping varieties of a variegated Kousa Dogwood for comparison.

BRIEF DESCRIPTION OF PHOTOGRAPHS

The accompanying colored photographs illustrate the overall appearance of the new weeping variegated Kousa Dogwood, showing the colors as true as it is reasonably possible to obtain in colored reproduction of this type.

PLANT DESCRIPTION

Figure 1:
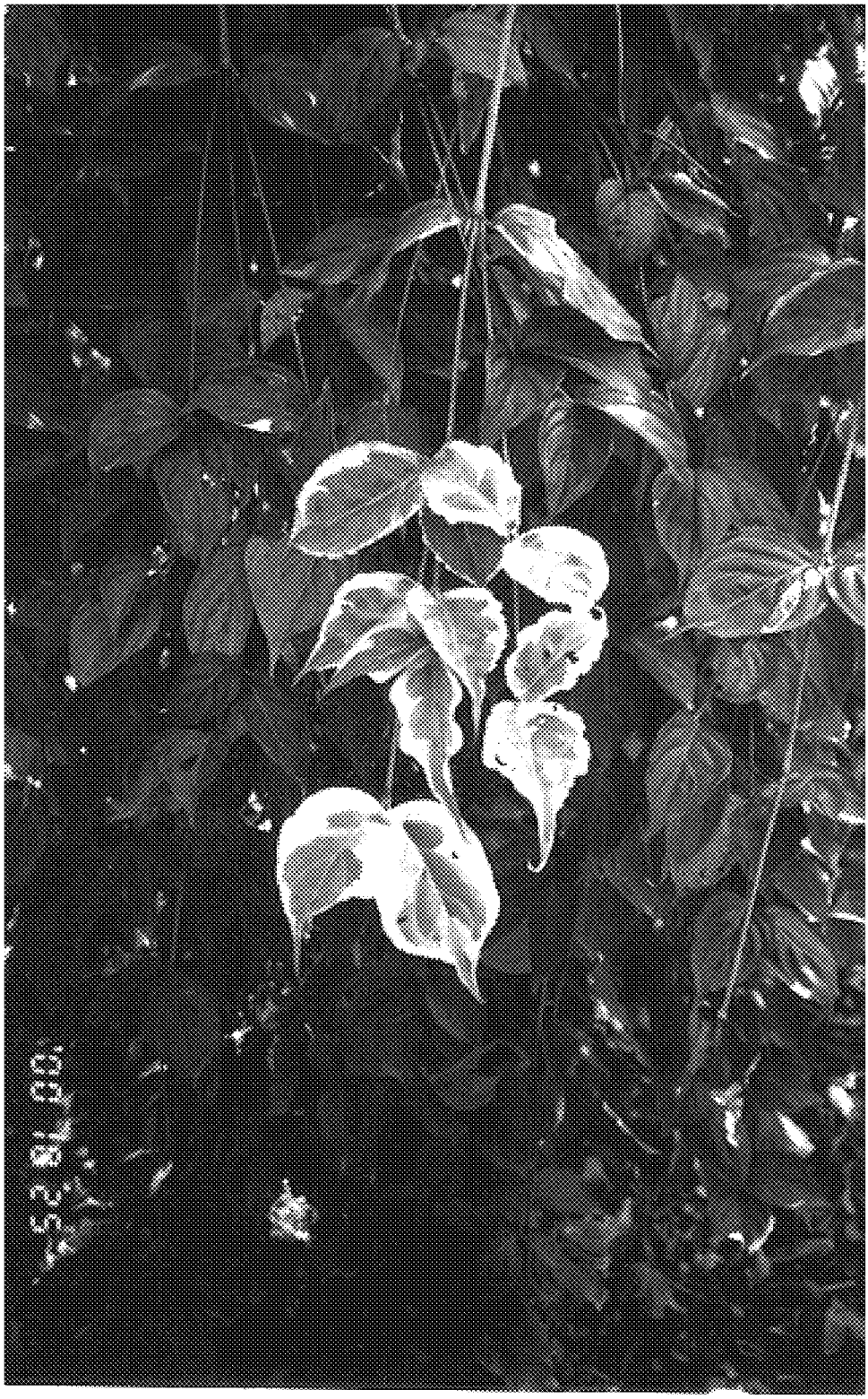
FIG. 1 shows the difference between the new variegated weeping mutation and the commonplace weeping variety on the same plant. Foliage colors in the photographs may appear different from the actual colors due to light reflectance.
Figure 2:
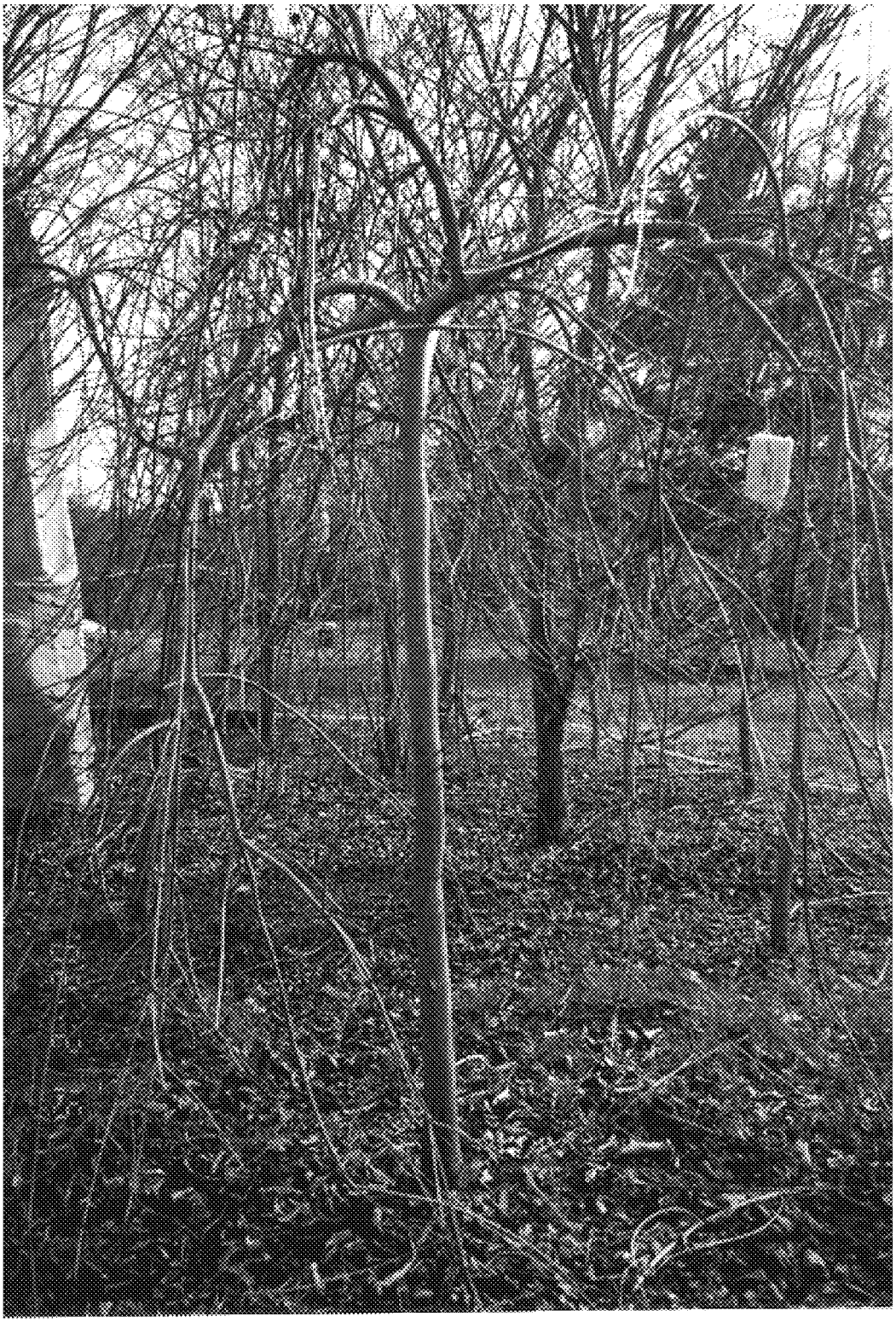
FIG. 2 shows the strong weeping habit of a dormant tree.
Figure 3:
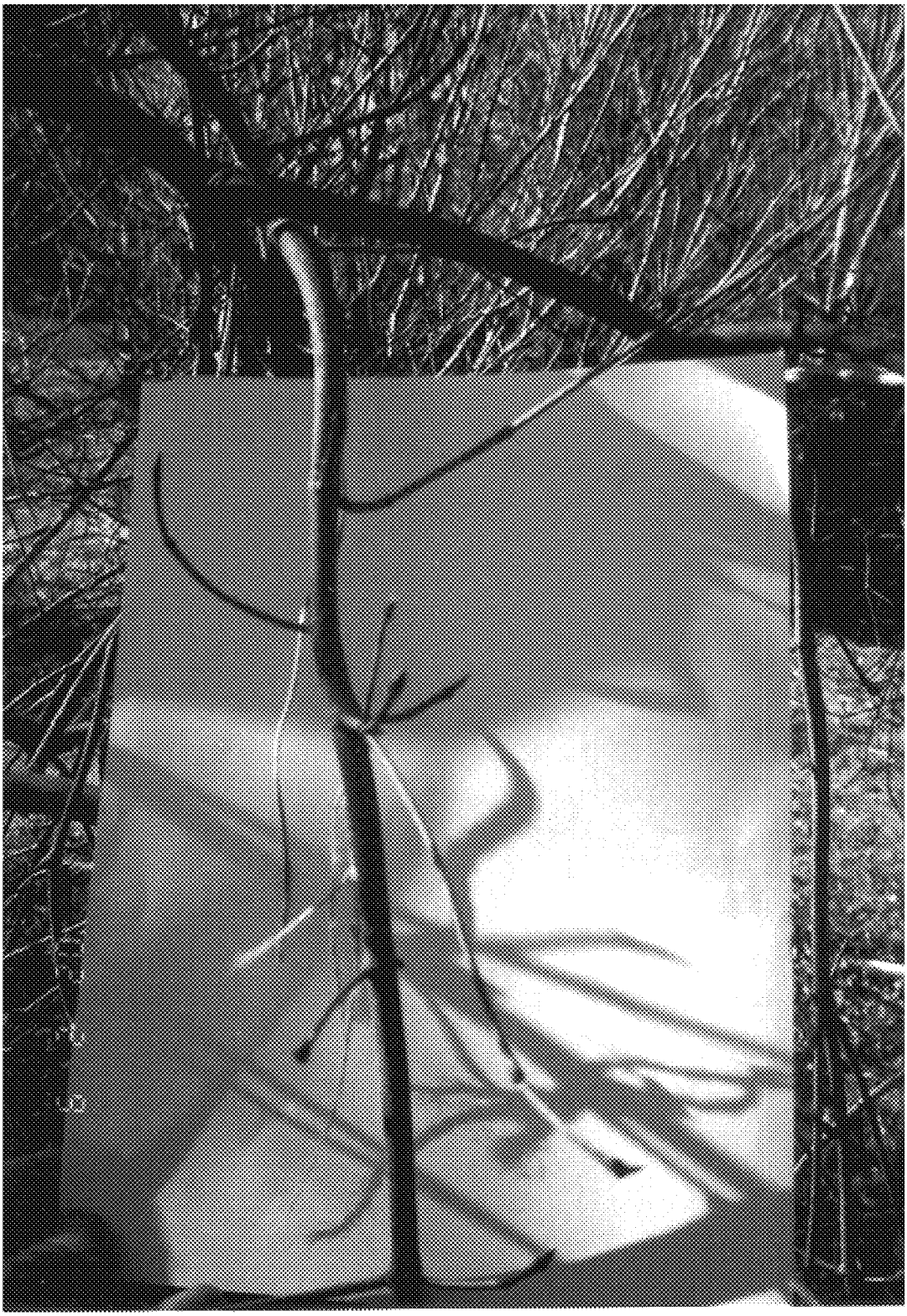
FIG. 3 shows a stem and flower bud.
Figure 4:
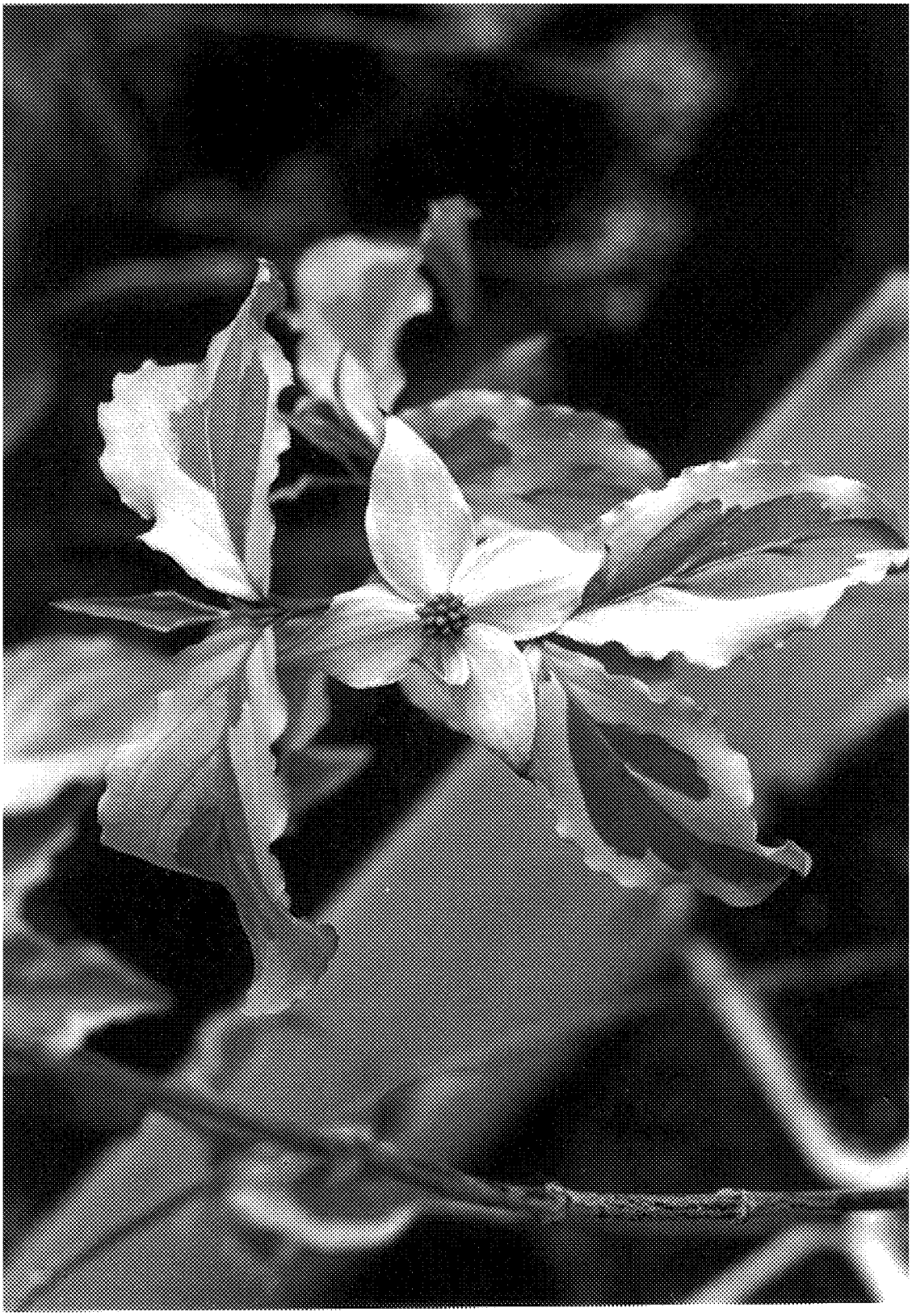
FIG. 4 shows a greenhouse forced flower.

Plant form and growth habit: Perennial deciduous tree, with strong weeping habit.

Vigor: Vigorous, similar to plants of the parent variety.

Plant size: All plants grafted on 24 to 36" Kousa understock in January and grown under outdoor Southeastern Pennsylvania conditions. Height and width unknown at this time, but it is assumed that the new cultivar will achieve height and width of a nonvariegated weeping variety.

Branching habit: Strongly weeping.

Main stem, or trunk discription: Like species when grafted on 3 foot to 5 foot standards and then allowed to weep; if grafted low, then leader must be staked and trained to desired height and then allowed to weep.

Bark texture: Smooth, bark color, gray: RHS 201B.

FOLIAGE DESCRIPTION

Leaves: Mature, opposite, simple, elliptical-ovate, 2" to 4" long, ¾" to 1¾" wide, acuminate, cuneate, undulating margins, center of leaf dark green RHS137C with greyed-yellow RHS160C irregular border. Upper and lower surfaces appear to be the same color except lower surface is duller. Variegation patterns are expressed on both surfaces of the leaves. Length of petiole ¼" on average. Occasional white splashes may randomly appear in the green center of the leaf area. Date of leaf-out mid April to early May. Gloss on leaves flat; hairs on upper surface absent, lower surface medium. Veins are easily visible. Color of immature leaves RHS144A — Variegation 151A. In the fall a greyed-red hue RHS181A becomes evident on the outer variegated area and becomes a deeper pink with colder temperatures, greyed-purple RHS187B. Color of autumn leaves red to purple.

Bud: Flower bud formed at the end of stem, ½" long, 3/16" wide, bud is flattened and globose at base with 2 valvate silky appressed pubescent bud scales forming a sharp apex. Bud color between RHS166A and 176A.

Bark: Exfoliation with age and forming a mottled mosaic of greyed-green RHS197C, greyed-orange 165B and brown 200D.

Size: Similar to species at; 10 yrs. old: height 8', width 5'.

Hardiness: Zone 5 to 8.

Habit: Pendulous and cascading. Rate: Medium to fast in early stages of growth (6 to 8" of growth on new grafts).

Flowers: Similar to species except for noted variegation.

*Type of inflorescence.*—Capitulum, ⅝" diameter.

*Bracts.*—4 bracts which are long and tapered to a point with noticeable marginal variegation during early growth period.

*Length and width of bract.*—⅞" long; ½" wide on average.

*Total width of flower.*—1 ¾" on average.

*Direction of inflorescence.*—Facing viewer. Color of bract RHS 157A (greenhouse grown and forced).

Blooming time: late May, one bloom per year, bracts persisting up to 6 weeks or longer. First bloom observed approximately late May; last bloom oberved early to mid July.

Fruit: Drupe, greyed-purple RHS185B.

*Diameter of fruit.*—¾ to 1".

*Seeds per drupe.*—4 to 10.

*Length of peduncle.*—2½".

*Color of peduncle.*—Pale green.

*Mature fruit.*—Observed early to mid October in Cedars, Pa.

Diseases and insects: None serious, typical of species.

I claim:

1. A new and distinct *Cornus Kousa* Dogwood tree named 'Kristin Lipka's Variegated Weeper', as illustrated and described.

* * * * *